(12) United States Patent
Dobrovolny

(10) Patent No.: US 7,507,825 B2
(45) Date of Patent: Mar. 24, 2009

(54) METHOD OF MANUFACTURING OF 7-ETHYL-10-[4-(1-PIPERIDINO)-1-PIPERIDINO]- CARBONYLOXY-CAMPTOTHECIN

(75) Inventor: Petr Dobrovolny, Brno (CZ)

(73) Assignee: Pliva-Lachema A.S., Brno (CZ)

( * ) Notice: Subject to any disclaimer, the term of this patent is extended or adjusted under 35 U.S.C. 154(b) by 240 days.

(21) Appl. No.: 10/567,472

(22) PCT Filed: Aug. 24, 2004

(86) PCT No.: PCT/CZ2004/000050

§ 371 (c)(1),
(2), (4) Date: Feb. 7, 2006

(87) PCT Pub. No.: WO2005/019223

PCT Pub. Date: Mar. 3, 2005

(65) Prior Publication Data

US 2006/0199961 A1 Sep. 7, 2006

(30) Foreign Application Priority Data

Aug. 26, 2003 (CZ) .......................... PV 2003-2305

(51) Int. Cl.
C07D 491/22 (2006.01)
C07D 401/04 (2006.01)
(52) U.S. Cl. ........................................ 546/48; 546/189
(58) Field of Classification Search ................... 546/48, 546/47, 189
See application file for complete search history.

(56) References Cited

U.S. PATENT DOCUMENTS

| | | | |
|---|---|---|---|
| 3,894,029 A | 7/1975 | Winterfeldt et al. | |
| 4,031,098 A | 6/1977 | Sugasawa | |
| 4,399,276 A | 8/1983 | Yokoyama et al. | |
| 4,399,282 A | 8/1983 | Miyasaka et al. | |
| 4,473,692 A | 9/1984 | Miyasaka et al. | |
| 4,604,463 A * | 8/1986 | Miyasaka et al. | 544/125 |
| 4,914,205 A | 4/1990 | Sawada et al. | |
| 5,061,800 A | 10/1991 | Yaegashi et al. | |
| 5,491,237 A | 2/1996 | Fang et al. | |
| 5,602,141 A | 2/1997 | Bedeschi et al. | |
| 5,734,056 A | 3/1998 | Burk et al. | |
| 5,843,954 A | 12/1998 | Yaegashi et al. | |
| 6,235,907 B1 | 5/2001 | Henegar et al. | |
| 6,310,210 B1 | 10/2001 | Ogawa et al. | |
| 6,403,569 B1 | 6/2002 | Achterrath | |
| 6,444,820 B1 | 9/2002 | Henegar et al. | |
| 6,743,918 B2 | 6/2004 | Yaegashi et al. | |
| 6,794,370 B2 | 9/2004 | Achterrath | |
| 7,126,000 B2 | 10/2006 | Ogawa et al. | |
| 7,151,179 B2 | 12/2006 | Lin et al. | |
| 2004/0235878 A1 | 11/2004 | Lin et al. | |
| 2005/0272757 A1 | 12/2005 | Naidu | |
| 2006/0199961 A1 | 9/2006 | Dobrovolny | |

FOREIGN PATENT DOCUMENTS

| | | |
|---|---|---|
| EP | 74770 | 3/1983 |
| EP | 88642 | 9/1983 |
| EP | 51289 | 4/1986 |
| EP | 74256 | 11/1986 |
| EP | 154584 | 2/1988 |
| EP | 154583 | 9/1988 |
| WO | WO96/31513 | 10/1996 |
| WO | WO2004/100897 | 11/2004 |
| WO | WO2005/019223 | 3/2005 |
| WO | WO2005/058910 | 6/2005 |

OTHER PUBLICATIONS

"Combination of Irinotecan (CPT-11) and 5-Fluorouracil with an analysis of cellular determinants of drug activity," Pavillard et al. Biochemical Pharmacology, vol. 56: 1315-1322, 1998.

"Clinical advances with topoisomerase I inhibitors in gastrointestinal malignancies," Armand, Jean-Pierre et al. Anti-Cancer Drugs 10 (Suppl. 1): S5-S12 (1999).

"Phase I/II study of escalating dose of CPT -11 in combination with LV5FU2 ("De Gramont" regimen) every 2 weeks in the treatment of colorectal cancer (CRC) after 5-FU failure," Ducreux, M. et al., Abstract 823, Proc. of Amer. Soc. Clin. Oncol. 16:234a (1997).

"Phase I study of a weekly schedule of irinotecan (CPT-11), high -dose folinic acid (FA) and 5-fluorouracil (5-FU) as first line chemotherapy (CT) in metastatic colorectal cancer: Final results," Vanhoefer, U. et al., Abstract 779, Proc. of Amer. Soc. Clin. Oncol. 17:202a (1998).

"Innotecan (CPT-11) in the treatment of gastrointestinal cancers," Nishiyama, M. Japanese J. Chemotherapy 46(8):292-296 (1998).

(Continued)

Primary Examiner—Charanjit S. Aulakh
(74) Attorney, Agent, or Firm—Foley & Lardner LLP

(57) ABSTRACT

The invention relates to the method of manufacturing of 7-ethyl-10-[4-(1-piperidino)-1-piperidino]-carbonyloxy-camptothecin by condensation of 7-ethyl-10-hydroxycamptothecin with 1-chlorocarbonyl-4-piperidinopiperidine hydrochloride in a polar aprotic solvent in the presence of 4-dimethylaminopyridine.

10 Claims, No Drawings

OTHER PUBLICATIONS

"CPT-11 (Irinotecan) and 5-Fluorouracil: a Promising Combination for Therapy of Colorectal Cancer," Saltz, L., et al., European J. Cancer 32A(Suppl. 3):S24-S31 (1996).

"Phase I/II study of CPT-11 in combination with LV5FU2 (De Gramont-Regimen) every 2 weeks for the treatment of colorectal cancer (CRC) after 5-FU failure," Seitz, J.F. et al., Abstract 261, Annals of Oncology 9 (Suppl. 2):68 (1998).

"Phase I study of a weekly schedule of irinotecan (CPT-11) in combination with high-dose folinic acid and 5-fluorouracil as first line chemotherapy in patients with advanced colorectal cancer," Vanhoefer, U. et al. Abstract 967, Proc. of Amer. Soc. Clin. Oncol. 16:272a (1997).

"Synthesis and Antitumor Activity of 20(S)-Camptothecin Derivatives. A-Ring-Substituted 7-Ethylcamptothecins and their E-Ring-Modified Water-Soluble Derivatives," Yaegashi et al. Chemical & Pharmaceutical Bulletin, vol. 42. No. 12:2518-2525(1994).

"Chemical Modification of an Antitumor Camptothecin: Synthesis and Antitumor Activity of 7-C-Substituted Camptothecins," Sawada et al. Chemical & Pharmaceutical Bulletin. vol. 39. No. 10: 2574-2580 (1991).

"Synthesis and Antitumor Activity of a A-Ring or E-Lactone Modified Water-Soluble Prodrugs of 20(S)-Camptothecin, Including Development of Irinotecan Hydrochloride Trihydrate," Sawada et al. Current Pharmaceutical Design. vol. 1 No. 1: 113-132 (1995).

Photodegradation reactions of CPT-II, a derivative of camptothecin. I: chemical structure of main degradation products in an aqueous solution, Akimoto et al. Drug Stability. vol. 1 No. 2.: 118-122 (1996).

"An Efficient Conversion of Camptothecin to 10-Hydroxycamptothecin," Wood et al. The Journal of Organic Chemistry. vol. 60. No. 17: 5739-5740 (1995).

"Synthesis and Antitumor of 20(S)-Camptothecin Derivatives: Carbamate-Linked, Water-Soluble Derivatives of 7-Ethyl-10-hydroxycamptothecin," Sawada, et al. Chemical & Pharmaceutical Bulletin, vol. 39. No. 6: 1446-1454 (1991).

"Synthesis and Antitumor Activity of 20(S)-Camptothecin Derivatives: A-Ring Modified and 7, 10-Disubstituted CAmptothecins," Sawada et al. Chemical & Pharmaceutical Bulletin, vol. 39. No. 12: 3183-3188 (1991).

* cited by examiner

METHOD OF MANUFACTURING OF 7-ETHYL-10-[4-(1-PIPERIDINO)-1-PIPERIDINO]- CARBONYLOXY-CAMPTOTHECIN

FIELD OF THE INVENTION

This invention relates to a method of manufacturing of 7-ethyl-10-[4-(1-piperidino)-1-piperidino]-carbonyloxy-camptothecin of formula I

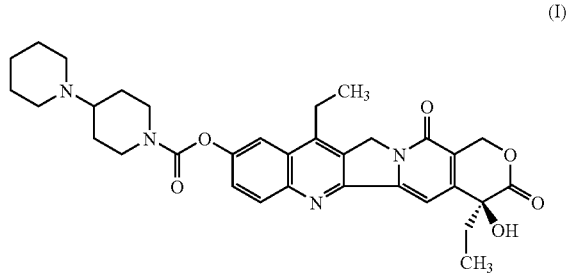

7-Ethyl-10-[4-(1-piperidino)-1-piperidino]-carbonyloxy-camptothecin, which is also known as irinotecan base, is used for manufacturing of the cytostatically active irinotecan hydrochloride trihydrate, a topoisomerase inhibitor which is used in treatment of lung and rectum cancer.

BACKGROUND OF THE INVENTION

7-Ethyl-10-[4-(1-piperidino)-1-piperidino]-carbonyloxy-camptothecin has been hitherto prepared by condensation of 7-ethyl-10-hydroxycamptothecin of formula

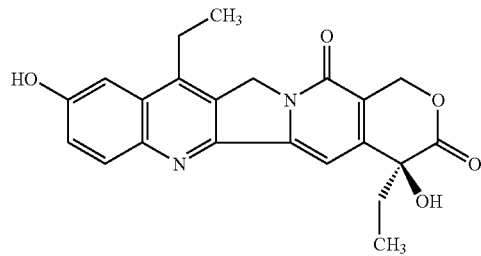

with 1-chlorocarbonyl-4-piperidinopiperidine hydrochloride of formula

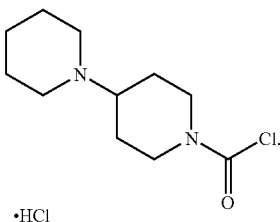

in pyridine at room temperature. This method has been described in the following documents: U.S. Pat. No. 4,604,463 (T. M. Kanagawa, S. Sawada, K. Nokata, E. Sugino, M. Mutai), issued on Aug. 5, 1986; S. Sawada, S. Okajima, R. Alyama, K. Nokata, T. Furuta, T. Yokokura, E. Sugino, K. Yamachuchi, T. Miyasaka, Chemical and Pharmaceutical Bulletin 1991. 39(6), 1446-1454; WO 96/31513 (K. E. Henegar. J. C. Sih), published on Oct. 10, 1996; U.S. Pat. No. 6,235,907 (K. E. Henegar, J. C. Sih), issued on May 22, 2001; U.S. Pat. No. 6,444,820 (K. E. Henegar. J. C. Sih), issued on Sep. 3, 2002.

SUMMARY OF THE INVENTION

The present invention relates to a method of manufacturing of 7-ethyl-10-[4-(1-piperidino)-1-piperidino]-carbonyloxy-camptothecin of formula I, characterized in that 7-ethyl-10-hydroxycamptothecin of formula II

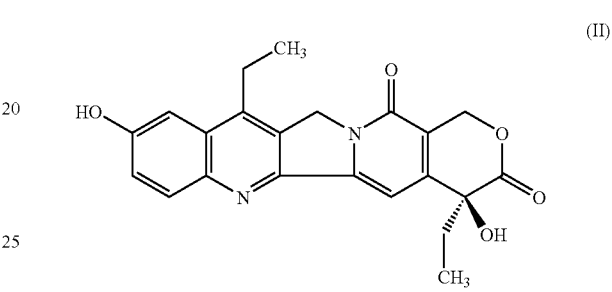

is condensed with 1-chlorocarbonyl-4-piperidinopiperidine hydrochloride of formula III

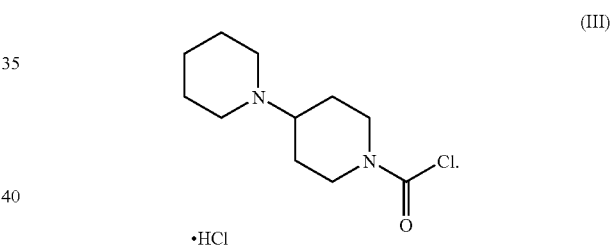

in a polar aprotic solvent such as acetonitrile and in the presence of 4-dimethylaminopyridine. The condensation proceeds in suspension, where the polar aprotic solvent dissolves only 4-dimethylaminopyridine whereas 7-ethyl-10-hydroxycamptothecin and 1-chlorocarbonyl-4-piperidinopiperidine hydrochloride in this polar aprotic solvent remain undissolved. The amount of 1-chlorocarbonyl-4-piperidinopiperidine hydrochloride employed in the condensation reaction is preferably 1.3 to 3 mol, more preferably 1.6 to 1.9 mol, per 1 mol of 7-ethyl-10-hydroxycamptothecin. The amount of 4-dimethylaminopyridine used in the condensation ranges preferably between 1.5 and 4 mol, more preferably between 1.8 and 2.2 mol, per 1 mol of 7-ethyl-10-hydroxycamptothecin. The amount of the polar aprotic solvent used in the condensation is preferably 400 to 600 mol, more preferably 430 to 460 mol, per mol of 7-ethyl-10-hydroxycamptothecin. The condensation is performed preferably at a temperature from 70 to 80° C., more preferably at 73 to 77° C.

After end of the condensation, the present ballast compounds, consisting of e.g. 4-dimethylaminopyridine, 4-piperidinopiperidine and urea, are removed by washing of the obtained irinotecan base by a polar aprotic solvent, preferably acetonitrile. The yield of the condensation is at least 94% and the obtained product contains at least 98% of the desired irinotecan base, as determined by high-performance liquid chromatography.

The main advantage of the method according to this invention consists in that the work-up of the reaction mixture after condensation proceeds only with negligible losses of the final product and that the condensation is not accompanied with coloured impurities.

EXAMPLES

Example 1

Into a beaker in a sonication bath are placed 10 g (0.0247 mol) of 7-ethyl-10-hydroxycamptothecin and 99 ml of acetonitrile. The obtained suspension is stirred in the sonication bath to homogeneity. Then the suspension is transferred quantitatively into a three-necked Keller flask equipped with a mechanical stirrer, thermometer and reflux condenser. Into the now empty beaker are now placed 6.2 g (0.0502 mol) of crystalline 4-dimethylaminopyridine and 40 ml of acetonitrile. The mixture is stirred until the crystalline portion dissolves. The obtained solution is then added quantitatively to the suspension of 7-ethyl-10-hydroxycamptothecin. Into the empty beaker are then added 13.6 g (0.0434 mol) of 1-chlorocarbonyl-4-piperidinopiperidine hydrochloride and 79 ml of acetonitrile and the suspension is stirred in the sonication bath until homogeneous. The obtained suspension is transferred quantitatively into the three-necked Keller flask already containing 7-ethyl-10-hydroxycamptothecin and 4-dimethylaminopyridine in acetonitrile, and 382 ml of acetonitrile is added to the mixture. The obtained reaction suspension in the Keller flask is stirred at 75° C. for 5 h. After 2 h the lightly yellow suspension becomes thicker and its colour turns into a coffee-white one, indicating thus correct course of the reaction. After 5 h, the suspension is cooled to 18 to 20° C., filtered and the filtration cake is washed with 300 ml of acetonitrile. After removing the acetonitrile by suction filtration, the obtained 7-ethyl-10-[4-(1-piperidino)-1-piperidino]-carbonyloxycamptothecin is dried at 60 to 65° C. to constant weight in a drier. This affords 14.1 g (yield 94.3%) of product which, according to high-performance liquid chromatography, contains 98.9% of 7-ethyl-10-[4-(1-piperidino)-1-piperidino]-carbonyloxycamptothecin.

The invention claimed is:

1. A method of preparation of 7-ethyl-10-[4-(1-piperidino)-1-piperidino]-carbonyloxy-camptothecin of formula I

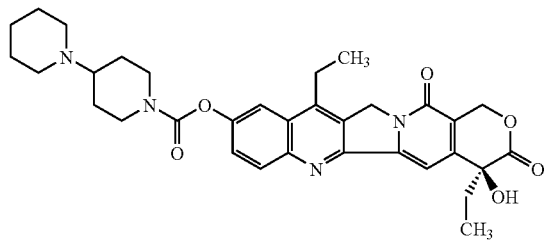

(I)

wherein 7-ethyl-10-hydroxycamptothecin of formula II

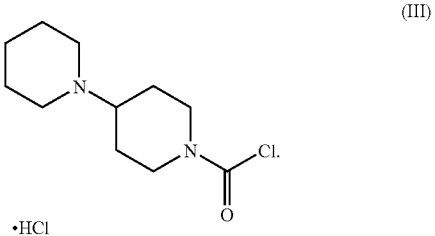

(II)

is subjected to a condensation reaction with 1-chlorocarbonyl-4-piperidinopiperidine hydrochloride of formula III (III)

in a polar aprotic solvent in the presence of 4-dimethylaminopyridine.

2. The method according to claim 1, wherein 1-chlorocarbonyl-4-piperidinopiperidine hydrochloride is employed in an amount of 1.3 to 3 mol, per 1 mol of 7-ethyl-10-hydroxycamptothecin.

3. The method according to claim 1, wherein 4-dimethylaminopyridine is employed in an amount of 1.5 to 4 mol, per 1 mol of 7-ethyl-10-hydroxycamptothecin.

4. The method according to claim 1, wherein the polar aprotic solvent is employed in an amount of 400 to 600 mol, per 1 mol of 7-ethyl-10-hydroxycamptothecin.

5. The method according to claim 1, wherein the condensation reaction is carried out at a temperature of 70 to 80° C.

6. The method according to claim 1, wherein the polar aprotic solvent is acetronitrile.

7. The method according to claim 2, wherein 1-chlorocarbonyl-4-piperidinopiperidine hydrochloride is employed in an amount of 1.6 to 1.9 mol of 7-ethyl-10-hydroxycamptothecin.

8. the method according to claim 1, wherein 4-dimethylaminopyridine is employed in an amount of 1.8 to 2.2 per 1 mol of 7-ethyl-10-hydroxycamptothecin.

9. The method according to claim 1, wherein the polar aprotic solvent is employed in an amount of 430 to 460 mol of 7-ethyl-10-hydroxycamptothecin.

10. The method according to claim 1, wherein the condensation reactin is carried out at a temperature of 73 to 77° C.

* * * * *